(12) United States Patent
Bismuth et al.

(10) Patent No.: US 8,942,349 B2
(45) Date of Patent: Jan. 27, 2015

(54) PROCESSING OF RADIOLOGICAL IMAGES TO DELETE MARKERS WITHOUT IMAGE DETERIORATION

(75) Inventors: Vincent Bismuth, Paris (FR); Sebastien Gorges, Versailles (FR)

(73) Assignee: General Electric Company, Schenectady, NY (US)

( * ) Notice: Subject to any disclaimer, the term of this patent is extended or adjusted under 35 U.S.C. 154(b) by 490 days.

(21) Appl. No.: 13/218,514

(22) Filed: Aug. 26, 2011

(65) Prior Publication Data

US 2012/0051497 A1 Mar. 1, 2012

(30) Foreign Application Priority Data

Aug. 26, 2010 (FR) ...................................... 10 56780

(51) Int. Cl.
*H05G 1/64* (2006.01)
*G06T 5/50* (2006.01)
*A61B 6/00* (2006.01)

(52) U.S. Cl.
CPC . *G06T 5/50* (2013.01); *A61B 6/482* (2013.01); *A61B 6/5241* (2013.01); *A61B 6/5258* (2013.01); *A61B 6/548* (2013.01); *A61B 6/4441* (2013.01); *G06T 2207/30004* (2013.01); *G06T 2207/10121* (2013.01); *G06T 2207/10144* (2013.01); *G06T 2207/20221* (2013.01); *G06T 2207/30204* (2013.01)
USPC ....................................... 378/98.12; 378/98.9

(58) Field of Classification Search
USPC ................................ 378/98.9, 98.12; 382/132
See application file for complete search history.

(56) References Cited

U.S. PATENT DOCUMENTS

| 4,868,857 A | * | 9/1989 | Dobbins, III | ................ 378/98.2 |
| 5,359,513 A | | 10/1994 | Kano et al. | |
| 5,910,972 A | | 6/1999 | Ohkubo et al. | |

OTHER PUBLICATIONS

Alvarez, Macovski, Lehmann et al: "Generalized image combinations in dual KVP digital radiography"; L.A. Lehmann, R.E. Alvarez, A. Macovski, W.R.Brody, N.J. Pelc, S.J. Riederer and A.L. Hall, Med. Phys. 8, 659 (1981), OI:10.1118/1.595025.
Bentum, M.J.; Arendsen, R.G.J.; Slump, C.H.; Mistretta, C.A.; Peppler, W.W.; Zink, F.E.; Lab. for Network Theory, Twente Univ. Design and realization of high speed single exposure dual energy image processing; Jun. 14-17, 1992; pp. 25-34.
Loeckx, D.; Maes, F.; Vandermeulen, D.; Suetens, P.; Medical Image Comput., University Hospital Gasthuisberg, Leuven, Belgium; "Temporal subtraction of thorax CR images using a statistical deformation model," Nov. 2003, vol. 22, issue 11, pp. 1490-1504.
Written Opinion and Search Report in connection with FR Patent Application No. 1056780 filed on Aug. 26, 2010, issued on Apr. 20, 2011.

* cited by examiner

*Primary Examiner* — Jurie Yun
(74) *Attorney, Agent, or Firm* — GE Global Patent Operation; Marc A. Vivenzio

(57) ABSTRACT

The disclosure generally relates to dual-energy imaging, and in particular, techniques to produce and process dual-energy images using a dual-energy imaging system. One embodiment provides a method for generating at least one image of a region of interest in a patient, the method comprising: obtaining at least two radiological images of the region of interest identified with at least one marker arranged on and/or around the patient, wherein a first image is acquired with a first X-ray energy and a second image is acquired with a second X-ray energy; and determining a final radiological image of the region of interest by linearly combining the two radiological images to obtain an image without the markers.

15 Claims, 3 Drawing Sheets

PROCESSING OF RADIOLOGICAL IMAGES TO DELETE MARKERS WITHOUT IMAGE DETERIORATION

BACKGROUND OF THE INVENTION

1. Field of the Invention

The disclosure generally relates to dual-energy imaging, and in particular, techniques to produce and process dual-energy images using a dual-energy imaging system.

2. Description of Related Art

In medical imaging, for the acquisition and processing of radiological images of a region of interest in a patient, it is often desirable to be able to identify particular points with precision. These may define a fixed reference point for example, or they may be joined to an object or anatomy whose movement it is desired to track.

To obtain these points, it is known to arrange markers on or around the patient. The arrangement of the markers depends on the region of the patient to be imaged. One problem is that these markers may mask some regions of interest and be detrimental to the quality of information that can be provided by the images.

BRIEF SUMMARY OF THE INVENTION

One aim of the embodiments of the invention is to delete the markers in a radiological image without deteriorating the quality of the image.

According to one first aspect, there is provided a method for generating at least one image of a region of interest in a patient, the method comprising: obtaining at least two radiological images of the region of interest identified with at least one marker arranged on and/or around the patient, wherein a first image is acquired with a first X-ray energy and a second image is acquired with a second X-ray energy; and determining a final radiological image of the region of interest by linearly combining the two radiological images to obtain an image without the markers.

According to a second aspect, there is provided an imaging system for obtaining radiological images comprising: a support configured to receive a patient to be examined; a source configured to emit an X-ray beam, connected to a C-arm; a detector, connected to the C-arm, wherein the detector is arranged facing the source and wherein the detector is configured to detect the X-rays emitted by the source; a control unit in communication with the C-arm, the source, and the detector, wherein the control unit is configured to control acquisition of images by setting parameters comprising a radiation dose and an angle position of the C-arm; and a processing system configured to receive acquired images and to linearly combine at least two radiological images to obtain a final radiological image without markers, the markers configured to locate a region of interest in a patient.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE SEVERAL VIEWS OF THE DRAWINGS

A full and enabling disclosure including the best mode thereof, to one of ordinary skill in the art, is set forth more particularly in the remainder of the specification, including reference to the accompanying figures wherein.

DETAILED DESCRIPTION OF THE INVENTION

Figure 1:
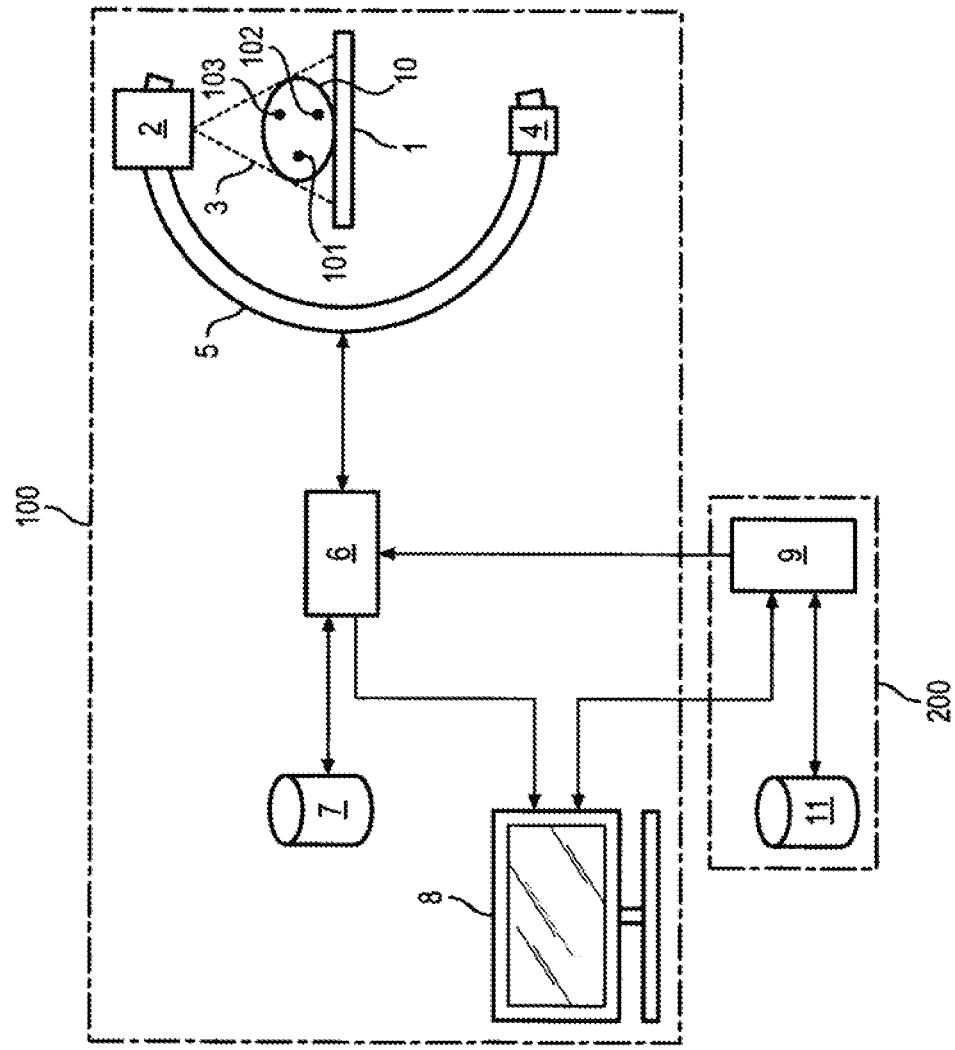
FIG. 1 schematically illustrates a medical imaging system according to an embodiment of the invention.

FIG. 1 schematically illustrates a medical imaging system 100 for the acquisition of radiological images. The medical imaging system 100 comprises a support 1 intended to receive a patient 10 to be examined, a source 2 intended to emit an X-ray beam 3, a detector 4 arranged facing the source 2 and configured to detect the X-rays emitted by the source 2, a control unit 6, a storage unit 7 and a display unit 8. The X-ray source 2 and the detector 4 are connected via a C-arm 5. The C-arm 5 is more commonly known as an archway. The C-arm 5 can be oriented along three degrees of freedom.

The detector 4 may be a semiconductor image sensor, for example comprising caesium iodide phosphor (scintillator) on a transistor/photodiode array in amorphous silicon. Other suitable detectors are: CCD sensor, direct digital detector which directly converts X-rays to digital signals. The detector 4 illustrated in FIG. 1 is planar and defines a planar image surface, other geometries evidently also being suitable.

The control unit 6 is connected to the C-arm 5 by wire or wireless connection. The control unit 6 is used to control the acquisition of images by setting several parameters such as the radiation dose to be emitted by the X-ray source and the angle position of the C-arm 5. The control unit 6 provides control over the position of the C-arm, i.e. the position of the source 2 relative to the detector 4. The control unit 6 may comprise a reader device (not shown) e.g. a diskette reader, CD-ROM or DVD-ROM reader, or connection ports to read the instructions of the processing method from an instruction medium (not shown) e.g. a diskette, CD-ROM, DVD-ROM, USB flash drive or more generally any removable memory medium or via a network connection.

The storage unit 7 is connected to the control unit 6 to record parameters and acquired images. It is possible to make provision for the storage unit 7 to be placed inside or outside the control unit 6. The storage unit 7 may be formed of a hard disk or SSD, or any other removable, rewriteable storage means (USB flash drives, memory cards etc . . . ). The storage unit 7 may be a ROM/RAM memory of the control unit 6, a USB flash drive, memory card or memory of a central server.

The display unit 8 is connected to the control unit 6 to display acquired images and/or information on acquisition control parameters. For example, the display unit 8 may be a computer screen, a monitor, flat screen, plasma screen or any other type of display device of known type. The display unit 8 allows the practitioner to control the acquisition of radiological images.

The medical imaging system 100 is coupled with a processing system 200. The processing system comprises a computing unit 9 and a storage unit 10. The processing system 200 receives acquired images stored in the storage unit 7 of the medical imaging system 100, on which it performs a certain number of processing operations described hereinafter. The transmission of data from the storage unit 7 of the medical imaging system 100 towards the computing unit 9 of the processing system 200 may take place via an internal or external computer network or by means of any suitable physical memory medium such as diskettes, CD-ROM, DVD-ROM, external hard disk, USB flash drive, SD card etc.

The computing unit 9 is one or more computers, for example, or one or more processors, one or more microcontrollers, one or more microcomputers, one or more programmable logic controllers, one or more application-specific integrated circuits, other programmable circuits, or other devices which include a computer such as a workstation. As a variant, the computing unit 9 may comprise a reader device (not illustrated) for example a diskette reader, CD-ROM or DVD-ROM reader, or connection ports to read the instructions of the processing method from an instruction medium (not illustrated) e.g. a diskette, CD-ROM, DVD-ROM, or USE flash drive or more generally any removable memory medium or via a network connection. In addition, the processing system comprises a storage unit 11 to store data generated by the computing unit 9. The computing unit 9 may be connected to the display unit 8 (as in FIG. 1) or to another display unit (not illustrated).

Figure 2:
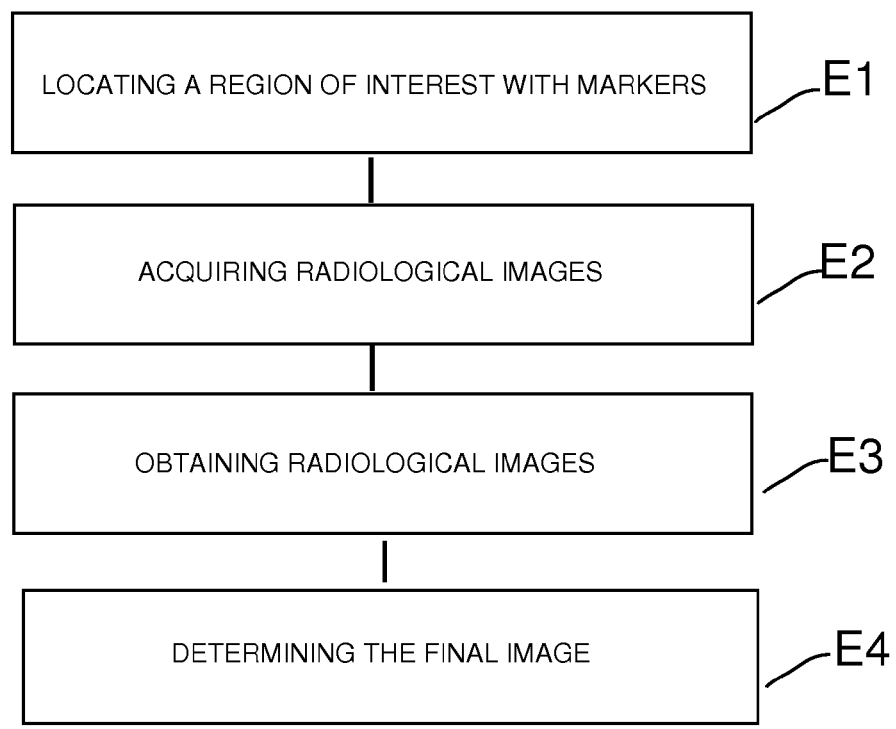
FIG. 2 illustrates steps of a method according to an embodiment of the invention.

Dual-energy medical imaging consists of acquiring images of one same part of anatomy with X-rays having different energies. The imaging protocol makes use of the absorption properties of the different imaged materials: human tissue, instruments used in interventional radiology, etc. FIG. 2 schematically illustrates the steps of a method for the processing of radiological images. The method comprises: locating a region of interest with markers E1, acquiring radiological images E2, obtaining radiological images E3, and determining the final image E4.

Figure 3:
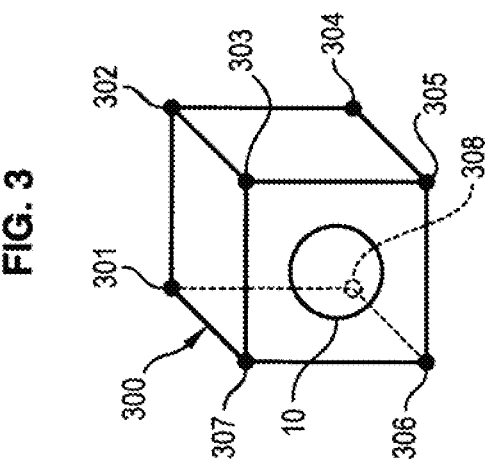
FIG. 3 illustrates a configuration of markers on a region of interest.

A region of interest is located on a patient E1 by arranging markers on or about the patient. FIG. 1 shows three markers 101, 102, 103 arranged on the region of interest of a patient 10, the markers being self-adhesive patches, for example, arranged on the skin, or a stereotaxy frame. FIG. 3 illustrates the region of interest 10 of a patient, identified by means of eight markers 301, 302, 303, 304, 305, 306, 307, 308 arranged at the eight corners of a cube 300. In practice, this is a configuration used to image a patient's head. The markers are such that they have different X-ray absorption properties from those of human tissues and/or when applicable of a contrast agent injected into the patient and/or of an instrument inserted into the patient.

In dual-energy imaging a material is characterized by the variability of its absorption in relation to the energy of the emitted radiation. Alvarez, Macovski, Lehmann et al: "*Generalized image combinations in dual KVP digital radiography*"; L. A. Lehmann, R. E. Alvarez, A. Macovski, W. R. Brody, N. J. Pelc, S. J. Riederer and A. L. Hall, Med. Phys. 8, 659 (1981), O1:10.1118/1.595025) have shown that the linear attenuation μ of a material can be expressed as a linear combination of two functions dependent on energy E:

$$\mu = \alpha_c \cdot f_c(E) + \alpha_p \cdot f_p(E).$$

The 2 constants $\alpha_c$ and $\alpha_p$ characterize the material and are notably dependent on the atomic number Z and the mass of the material. A material is therefore chosen whose constants $\alpha_c$ and $\alpha_p$ are significantly different from those of human tissues and/or iodine and/or medical instruments. This choice may be guided by examining masses and atomic numbers.

Radiological images are acquired E2 by means of the medical imaging system, one image being acquired with a first X-ray energy, the following being acquired with a second X-ray energy. The interval between two successive images typically lies between 33 ms and one second, depending upon the application. Preferably, the two images are acquired at the two different energies so that there is no significant movement between these two images. For example, for cardiac applications a very short time interval will be sought, shorter than the standard intervals of 33 ms, optionally at the time of the cardiac phase when the heart is the most static. On the other hand, for neuro-radiology applications in which movements are less rapid, longer time intervals can be used.

Figure 4:
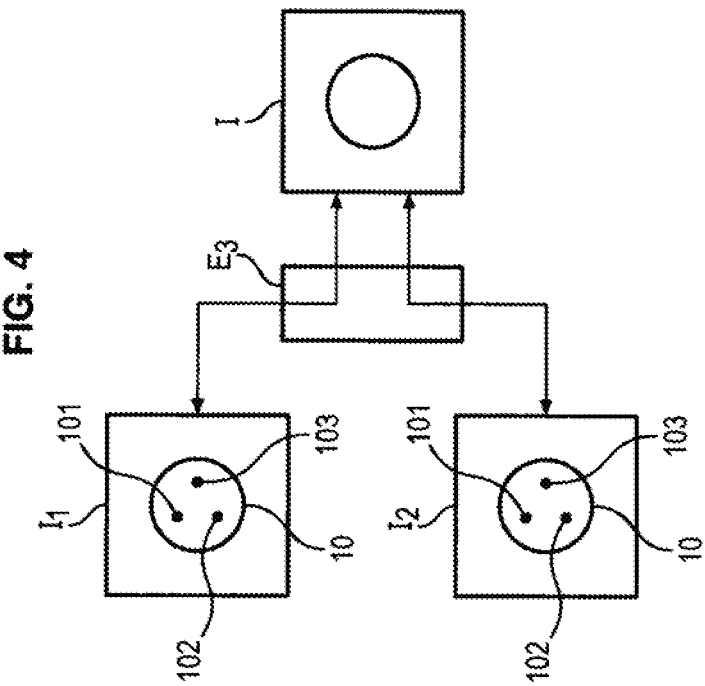
FIG. 4 illustrates a step of a method according to an embodiment of the invention.

FIG. 4 schematically illustrates two images $I_1$ and $I_2$ in which the region of interest 10 is shown with three markers 101, 102, 103. The images $I_1$ and $I_2$ differ in that the markers 101, 102, 103 have a different appearance. They are contrasted to a greater or lesser extent. This difference in contrast is due to the absorption of the markers 101, 102, 103 which varies in relation to the energy used for acquisition E2.

Obtaining radiological images E3 consists either of acquiring the different radiological images, or retrieving radiological images that were stored after acquisition. These can be stored in the storage unit 7 of the medical imaging system.

Determination E4 of the final image consists of determining the final image by combining the images $I_1$ and $I_2$ (frequently from their logarithms), for example using $I = \alpha \log I_1 + \beta \log I_2$ in which $I_1$ and $I_2$ are radiological images acquired using the medical imaging system with different absorbencies, $\alpha$ and $\beta$ are constants which can be determined in relation to the constituent material of the markers it is desired to delete.

There is abundant literature on the subject and the methods are numerous and varied, according to desired precision and image-related assumptions. For example, reference may be made to "Imagerie du sein multi spectrale avec produit de contraste; Thèse de doctorat; Sylvie Puong; 2008" (*Multispectral breast imaging with contrast agent; Doctoral thesis; Sylvie Puong*, 2008) for the prior art of all these methods. FIG. 4 illustrates the final image I in which the markers 101, 102, 103 have been deleted. The final image I is not deteriorated by this linear combination, only the markers are deleted.

The method described in the foregoing can be implemented using a computer program comprising machine instructions for this purpose. The computer program can be stored on any ad hoe medium of known type, for example: hard disk, CD-ROM, DVD-ROM, diskette, USB flash drive, SD card. These storage means may also be kept on a local or remote server.

What is claimed is:

1. A method for generating at least one image of a region of interest in a patient, the method comprising:
   obtaining at least two radiological images of the region of interest with a medical imaging system, wherein the at least two radiological images of the region of interest are identified with at least one marker arranged on and/or around the patient, wherein a first image was acquired with a first X-ray energy and a second image was acquired with a second X-ray energy; and
   determining with a processing system of the medical imaging system a final radiological image of the region of interest by linearly combining the at least two radiological images of the region of interest obtained by the medical imaging system to further obtain a final radiological image of the region of interest without the markers.

2. The method according to claim 1 further comprising locating in space the region of interest by arranging the at least one marker on and/or around the patient.

3. The method according to claim 2, wherein the at least one marker is comprised of a material with different absorbency properties than those of human tissues and/or optionally a contrast agent injected into the patient and/or an instrument inserted into the patient.

4. The method according to claim 1, wherein the final radiological image is obtained with the following linear combination:

$$I=\alpha \log I_1 + \beta \log I_2,$$

wherein I is the final image, $I_1$ and $I_2$ are the radiological images acquired with the medical imaging system at different energies, and $\alpha$ and $\beta$ are constants dependent on the respective material of the at least one marker and spectra of the X-rays used.

5. The method according to claim 1, wherein the radiological images are fluoroscopic images acquired in real-time.

6. The method according to claim 1, wherein the radiological images are images previously acquired and stored in a memory unit of the medical imaging system.

7. An imaging system for obtaining at least one final radiological image of a region of interest in a patient linearly combined from at least two radiological images, wherein at least one marker is arranged on and/or around the patient at the time the at least two radiological images are obtained, the imaging system comprising:
- a support configured to receive a patient to be examined;
- a source configured to emit an X-ray beam, wherein the source is connected to a C-arm;
- a detector, connected to the C-arm, wherein the detector is arranged facing the source and wherein the detector is configured to detect the X-rays emitted by the source;
- a control unit operatively connected to the C-arm, the source, and the detector, wherein the control unit is configured to control acquisition of images by setting parameters; and
- a processing system configured to receive the at least two radiological images acquired by the imaging system and to linearly combine the at least two radiological images to obtain the at least one final radiological image of a region of interest without markers.

8. The imaging system according to claim 7, further configured to obtain a first image acquired with a first X-ray energy and a second image acquired with a second X-ray energy.

9. The imaging system according to claim 8, wherein the processing system linearly combines the at least two radiological images with the following linear combination:

$$I=\alpha \log I_1 + \beta \log I_2,$$

wherein I is the final image, $I_1$ and $I_2$ are the radiological images acquired with the medical imaging system at different energies, and $\alpha$ and $\beta$ are constants dependent on the respective material of the at least one marker and spectra of the X-rays used.

10. The imaging system according to claim 7, wherein the processing system comprises a memory unit and the processing system is further configured to linearly combine at least two radiological images previously acquired and stored in the memory unit.

11. The imaging system according to claim 7, wherein the detector is chosen from the group consisting of a semiconductor image sensor, a CCD sensor, and a direct digital detector.

12. The imaging system according to claim 7, wherein the control unit is operatively connected to the C-arm, the source, and the detector by a wire and/or wireless connection.

13. The imaging system according to claim 7, further comprising a storage unit connected to the control unit configured to record the parameters and/or the acquired images.

14. The imaging system according to claim 7, further comprising a display connected to the control unit and configured to display the acquired images and/or information on acquisition control parameters.

15. The imaging system according to claim 7, wherein the radiological images are fluoroscopic images acquired in real-time.

* * * * *